United States Patent
Ishikawa

(10) Patent No.: US 11,366,336 B2
(45) Date of Patent: Jun. 21, 2022

(54) TORIC OPHTHALMIC LENS

(71) Applicant: Kowa Company, Ltd., Nagoya (JP)

(72) Inventor: Haruo Ishikawa, Nagoya (JP)

(73) Assignee: Kowa Company, Ltd., Nagoya (JP)

( * ) Notice: Subject to any disclaimer, the term of this patent is extended or adjusted under 35 U.S.C. 154(b) by 243 days.

(21) Appl. No.: 16/467,473

(22) PCT Filed: Dec. 6, 2017

(86) PCT No.: PCT/JP2017/043769
§ 371 (c)(1),
(2) Date: Jun. 6, 2019

(87) PCT Pub. No.: WO2018/105640
PCT Pub. Date: Jun. 14, 2018

(65) Prior Publication Data
US 2019/0328509 A1    Oct. 31, 2019

(30) Foreign Application Priority Data

Dec. 7, 2016    (JP) .............................. JP2016-237403

(51) Int. Cl.
*G02C 7/02*    (2006.01)
*G02C 7/04*    (2006.01)
(Continued)

(52) U.S. Cl.
CPC .............. *G02C 7/02* (2013.01); *A61F 2/1645* (2015.04); *G02C 7/024* (2013.01); *G02C 7/04* (2013.01);
(Continued)

(58) Field of Classification Search
CPC . G02C 7/02; G02C 7/024; G02C 7/04; G02C 7/06; G02C 2202/22; A61F 2/1645;
(Continued)

(56) References Cited

U.S. PATENT DOCUMENTS 4,781,452 A * 11/1988 Ace ..................... B24B 9/148
351/159.74
5,173,723 A    12/1992 Volk
(Continued)

FOREIGN PATENT DOCUMENTS

CN    102656504 A    9/2012
EP    2111822 A2    10/2009
(Continued)

OTHER PUBLICATIONS

International Preliminary Report on Patentability received in International Patent Application No. PCT/JP2017/043769 dated Jun. 13, 2019.

(Continued)

*Primary Examiner* — Jordan M Schwartz
(74) *Attorney, Agent, or Firm* — Knobbe, Martens, Olson & Bear, LLP

(57) ABSTRACT

To realize a toric ophthalmic lens including an edge that makes it possible to design a lens contributing to secondary cataract prevention without deteriorating a degree of freedom of lens design. The toric ophthalmic lens is a toric ophthalmic lens in which, in a top view of an optical portion, a substantially flat portion having a substantially fixed edge thickness of the optical portion is provided to overlap a steep meridian of a toric surface of the optical portion.

9 Claims, 5 Drawing Sheets

(51) Int. Cl.
*A61F 2/16* (2006.01)
*A61B 3/103* (2006.01)

(52) U.S. Cl.
CPC ........ *A61B 3/1035* (2013.01); *G02C 2202/22* (2013.01)

(58) Field of Classification Search
CPC .......... A61F 2/1613; A61F 2002/16905; A61F 2002/1699
See application file for complete search history.

(56) References Cited

U.S. PATENT DOCUMENTS

| | | | | |
|---|---|---|---|---|
| 5,478,824 | A | * | 12/1995 | Burns ................ C08G 18/758 351/159.48 |
| 6,176,578 | B1 | * | 1/2001 | Clutterbuck ............ G02C 7/04 351/159.21 |
| 6,666,887 | B1 | | 12/2003 | Callahan et al. |
| 2005/0274241 | A1 | * | 12/2005 | Mandell .................... B23B 5/00 82/1.11 |
| 2008/0218689 | A1 | * | 9/2008 | Blum .................... G02C 7/061 351/159.42 |
| 2009/0030514 | A1 | | 1/2009 | Niwa et al. |
| 2009/0132041 | A1 | * | 5/2009 | Fiala .................... A61F 2/1613 623/6.23 |
| 2010/0041318 | A1 | | 2/2010 | Schneider et al. |
| 2010/0211169 | A1 | | 8/2010 | Stanley et al. |
| 2011/0149229 | A1 | | 6/2011 | Gergligand et al. |
| 2012/0127425 | A1 | * | 5/2012 | Goebel Quintana ....................... B29D 11/00432 351/159.61 |
| 2015/0351901 | A1 | * | 12/2015 | Stoy ...................... A61F 2/1648 623/6.34 |
| 2016/0296662 | A1 | | 10/2016 | Stoy et al. |
| 2017/0045756 | A1 | | 2/2017 | Ishikawa |
| 2018/0203251 | A1 | | 7/2018 | Goto et al. |

FOREIGN PATENT DOCUMENTS

| | | |
|---|---|---|
| EP | 2319457 A1 | 5/2011 |
| JP | 2005-506875 A | 3/2005 |
| JP | 2010-188131 A | 9/2010 |
| JP | 4945558 B2 | 6/2012 |
| JP | 2016-508062 A | 3/2016 |
| JP | 6002357 B1 | 10/2016 |
| WO | WO 2006-123427 A1 | 11/2006 |
| WO | WO 2006/136424 A1 | 12/2006 |
| WO | WO 2008/096007 A2 | 8/2008 |
| WO | WO 2014-020634 A1 | 2/2014 |
| WO | WO 2015/078271 A1 | 6/2015 |
| WO | WO 2015-136997 A1 | 9/2015 |

OTHER PUBLICATIONS

International Search Report in International Patent Application No. PCT/JP2017/043769, dated Mar. 13, 2018.
Extended European Search Report issued in corresponding EP application No. 17877631.6, dated Jul. 15, 2020.

* cited by examiner

TORIC OPHTHALMIC LENS

FIELD

The present invention relates to a toric ophthalmic lens for astigmatism correction.

BACKGROUND

Examples of ophthalmic lenses for astigmatism correction include eyeglasses, contact lenses, and intraocular lenses. These ophthalmic lenses have an optical surface called toric surface. The toric surface indicates a surface shape of a lens, curvature radiuses of at least two meridians of which are different, like a rugby ball or a side surface of a doughnut. The lens including the toric surface is called toric lens (annular lens).

A difference is caused in refractive power of the lens by the toric surface in directions orthogonal to each other set on the surface. Astigmatism can be corrected using the difference in the refractive power. A technique for more flexibly designing a shape of a lens surface and a technique for stabilizing a position of an intraocular lens in an eye have been proposed (PTL 1 and 2). A technique for configuring a connecting portion of an optical portion and a supporting portion to advantageously suppress occurring of a secondary cataract has also been proposed (PTL 3). A technique for defining a toric surface with a formula has also been proposed (PTL 4).

CITATION LIST

Patent Literature

[PTL 1] U.S. Pat. No. 5,173,723
[PTL 2] WO 2015/136997
[PTL 3] WO 2006/123427
[PTL 4] Japanese Patent No. 4945558

SUMMARY

Technical Problem

However, in a conventional ophthalmic lens for astigmatism correction, it is not assumed that the thickness of an edge of the lens is controlled. Therefore, it is likely that the thickness of the edge hinders design of an intraocular lens from the viewpoint of secondary cataract prevention. That is, it is desired that the edge thickness is equal to or larger than a predetermined thickness from the viewpoint of the secondary cataract prevention. However, the center thickness of the lens is large if a lens shape is simply decided based on the edge thickness. Therefore, insertion through a small incision is difficult. It is likely that a burden during the insertion is increased.

A technique according to the present disclosure has been made in view of the above-described circumstances, and an object of the present disclosure is to realize a toric ophthalmic lens that makes it possible to design a lens contributing to secondary cataract prevention without deteriorating a degree of freedom of lens design, that is, a toric ophthalmic lens that has an edge having thickness with which a secondary cataract prevention effect can be expected and does not have an unnecessarily large center thickness.

Solution to Problem

In a toric ophthalmic lens of the present disclosure, in a top view of an optical portion, a substantially flat portion having a substantially fixed edge thickness of the optical portion is provided to overlap a steep meridian of a toric surface of the optical portion. Consequently, in the past, there is a concern that the edge thickness in a steep meridian direction decreases and, if a supporting portion is provided in a portion where the edge thickness decreases, a force for pressing the optical portion against a posterior capsule in an eye cannot be stably obtained. However, with the toric ophthalmic lens of the present disclosure, even if the supporting portion is provided in the portion, since a predetermined edge thickness is secured, the force for pressing the optical portion against the posterior capsule can be stably obtained. Lens design having a higher degree of freedom is possible from the viewpoint of preventing a secondary cataract. The edge thickness of the substantially flat portion is smaller than the edge thickness of the optical portion overlapping a flat meridian of the toric surface in the top view and is larger than the edge thickness of the optical portion overlapping the steep meridian of the toric surface in the top view when the substantially flat portion is formed as the toric surface.

Further, the substantially flat portion may be formed by replacing a region of the toric surface where thickness is smaller than a predetermined minimum thickness in the toric ophthalmic lens with a plane, the thickness of which is the minimum thickness. The substantially flat portion may be formed as a gentle inclined surface or a curved surface or a form obtained by combining the inclined surface and the curved surface.

In a top view of an optical portion of a toric ophthalmic lens, a substantially flat portion in which an edge thickness h(r) of the optical portion in a position where a distance from a lens center is r is given by Expressions (1) and (2) may be provided.

[Math. 1]
$$h(r) \geq H \tag{1}$$

[Math. 2]
$$H(\text{High}) < H < H(\text{Low}) \tag{2}$$

wherein, H(High) represents an edge thickness of a portion overlapping a steep meridian of the toric ophthalmic lens and H(Low) represents an edge thickness of a portion overlapping a flat meridian of the toric ophthalmic lens. H is equivalent to a predetermined minimum thickness.

A sectional shape in any meridian direction on a lens surface of the toric ophthalmic lens may be represented by an expression including:

[Math. 3]
$$Z = \frac{cr^2}{1 + [1 - c^2 r^2 (k+1)]^{1/2}} + A(\theta) r^2 + B(\theta) r^4 \tag{3}$$

wherein, c represents a paraxial curvature in the toric ophthalmic lens, r represents a distance from the lens center of the toric ophthalmic lens, k represents a conic constant of a surface rotationally symmetrical to a lens optical axis in the toric ophthalmic lens, c, r, and k are common concerning a meridian direction on the lens surface, and A(θ) and B(θ) are given by Expressions (4) and (5).

[Math. 4]
$$A(\theta) = a_{2x} \cos^2 \theta + a_{2y} \sin^2 \theta \tag{4}$$

[Math. 5]

$$B(\theta) = a_{4x}\cos^4\theta + a_{2x2y}\cos^2\theta\sin^2\theta + a_{4y}\sin^4\theta \quad (5)$$

wherein, H(High) represents an edge thickness of a portion overlapping the steep meridian when the toric ophthalmic lens is designed using Expressions (4) and (5) and H(Low) represents an edge thickness of a portion overlapping the flat meridian when the toric ophthalmic lens is designed using Expressions (4) and (5).

Further, in a top view of the toric ophthalmic lens, width of the substantially flat portion in a direction from an edge toward a lens center of the toric ophthalmic lens may be set to 0.05 mm or more and 0.5 mm or less. In the top view of the toric ophthalmic lens, a range of an angle in which the substantially flat portion is formed viewed from the lens center of the toric ophthalmic lens may be set to 20° or more and 70° or less across the steep meridian (10° or more and 35° or less with respect to the steep meridian). In general, an optical portion diameter of an intraocular lens is ϕ5 mm to 7 mm. Therefore, in the top view of the toric ophthalmic lens, width L of the substantially flat portion in the direction from the edge toward the lens center of the toric ophthalmic lens may satisfy a condition (1/100 of the optical portion diameter)≤L≤(1/10 of the optical portion diameter).

In a toric ophthalmic lens of the present disclosure, in a top view of an optical portion, a surface continuous to an edge of the optical portion and a toric surface of the optical portion may be provided. An edge thickness of the optical portion on the continuous surface may be substantially fixed. The continuous surface may be provided to overlap a steep meridian of the toric surface of the optical portion.

Advantageous Effects of Invention

According to the technique of the present disclosure, it is possible to realize a toric ophthalmic lens including an edge that makes it possible to design a lens contributing to secondary cataract prevention without deteriorating a degree of freedom of lens design.

DESCRIPTION OF EMBODIMENTS

Figure 1:
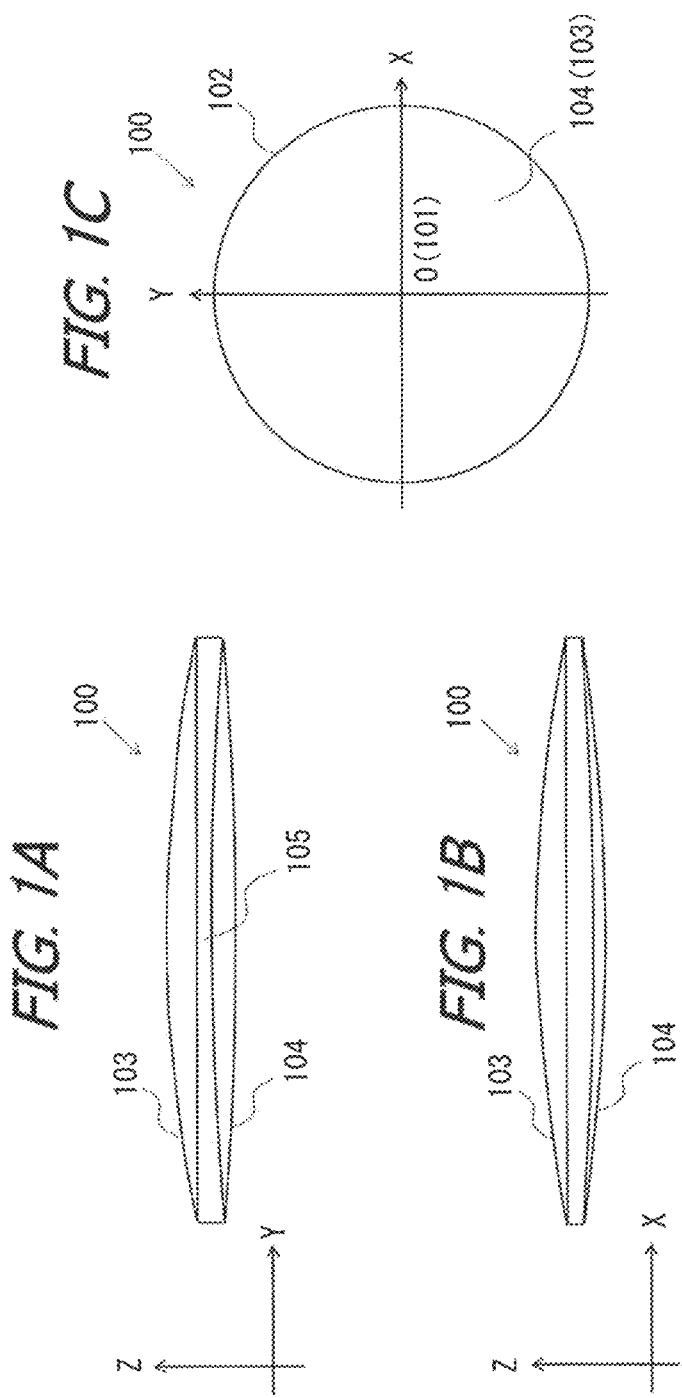
FIG. 1A is a first schematic diagram illustrating an example of a conventional toric intraocular lens.
FIG. 1B is a second schematic diagram illustrating an example of a conventional toric intraocular lens.
FIG. 1C is a third schematic diagram illustrating an example of a conventional toric intraocular lens.

An embodiment of the present invention is explained below. Note that a toric intraocular lens is explained in the following explanation. However, the present invention is not limited to the toric intraocular lens and can also be applied to various toric ophthalmic lenses such as an eyeglass lens.

In the toric intraocular lens, a difference is caused in refractive power of the lens by a toric surface in directions orthogonal to each other (a first meridian direction and a second meridian direction) set on the surface. Astigmatism can be corrected using the difference in the refractive power. In general, the difference in the refractive power is called columnar reflective power. On the toric surface, a meridian in a direction in which the refractive power is large is called steep meridian and a meridian in a direction in which the refractive power is small is called flat meridian.

First, a technique serving as a premise of the present invention is explained. In this embodiment, a lens surface is defined by the following Expression (6) to manufacture an intraocular lens. Note that a first term of Expression (6) defines a lens surface rotationally symmetrical with respect to an optical axis of the lens. Second and subsequent terms define a toric surface.

[Math. 6]

$$Z = \frac{cr^2}{1 + [1 - c^2 r^2 (k+1)]^{1/2}} + a_{2x} X^2 + a_{2y} Y^2 + a_{4x} X^4 + a_{2x2y} X^2 Y^2 + a_{4y} Y^4 + \ldots \quad (6)$$

wherein, c represents a curvature of a reference plane of the rotational symmetry of the lens before the toric surface defined by the second and subsequent terms of Expression (6) is added. X and Y represent distances from a lens center in a first direction and a second direction, for example, distances from the lens center in a steep meridian direction and a flat meridian direction. In Expression (6), r represents a distance in a radial direction ($r^2=X^2+Y^2$), k represents a conic constant of the reference plane of the rotational symmetry before the toric surface defined by second and subsequent terms of Expression (6) is added, and c, r, and k are common in the X direction and the Y direction. In Expression (6), a represents a parameter for adding the toric surface. The second and subsequent terms of Expression (6) represent terms at the time when $(X^2+Y^2)^n$ (n=1, 2, ... ) is developed. Coefficients of the second and subsequent respective terms represent parameters for adding the toric surface. Note that the first term of Expression (6) is an example of a predetermined definitional equation for defining a lens surface of rotational symmetry with respect to the optical axis of the lens. The first term may be another equation if the equation is an equation defining the lens surface equivalent to the first term of Expression (6).

The lens surface can be defined over the entire lens when the above expression is used. Consequently, it is possible to define the lens surface with a high degree of freedom compared with the past. In particular, a shape in a direction (e.g., a direction in which X=Y) other than the X direction and the Y direction that cannot be defined by the conventional expression as explained above can also be freely defined.

The first term of Expression (6) is the same form as an expression of a spherical lens or an expression of an aspherical lens by only a conic constant. Therefore, when the toric intraocular lens is designed using Expression (6), a base shape of the toric intraocular lens can be a rotationally symmetric lens as in the past. Therefore, the toric intraocular lens manufactured by performing lens design using Expression (6) can be loaded in a conventional inserter as well without a problem.

degree of freedom of parameters for defining the toric surface of the toric intra ocular lens increases. It is possible to design a lens surface shape for more suitably correcting various aberrations than in the past.

Subsequently, concerning Expression (6), an expression formula of a sectional shape in any direction (at an angle θ) of an optical surface of the lens is derived. As an example, the case of maximum order of 4th order is considered. If $x=r\cos\theta$ and $y=r\sin\theta$ in Expression (6), Expression (6) is transformed to obtain Expression (7) as follows.

[Math. 7]

$$Z = \frac{cr^2}{1+[1-c^2r^2(k+1)]^{1/2}} + a_{2x}X^2 + a_{2y}Y^2 + a_{4x}X^4 + a_{2x2y}X^2Y^2 + a_{4y}Y^4 \quad (7)$$

$$= \frac{cr^2}{1+[1-c^2r^2(k+1)]^{1/2}} + (a_{2x}\cos^2\theta + a_{2y}\sin^2\theta)r^2 +$$

$$(a_{4x}\cos^4\theta + a_{2x2y}\cos^2\theta\sin^2\theta + a_{4y}\sin^4\theta)r^4$$

$$= \frac{cr^2}{1+[1-c^2r^2(k+1)]^{1/2}} + A(\theta)r^2 + B(\theta)r^4.$$

Herein,

[Math. 8]

$$A(\theta) = a_{2x}\cos^2\theta + a_{2y}\sin^2\theta,\ B(\theta) = a_{4x}\cos^4\theta + a_{2x2y}\cos^2\theta\sin^2\theta + a_{4y}\sin^4\theta$$

[Math. 9]

$$A(\theta) = \frac{1}{2}[a_{2x} + a_{2y} + (a_{2x} - a_{2y})\cos 2\theta],$$

$$B(\theta) = \frac{1}{8}[(3a_{4x} + a_{2x2y} + 3a_{4y}) + 4(a_{4x} - a_{4y})\cos 2\theta + (a_{4x} - a_{2x2y} + a_{4y})\cos 4\theta].$$

Note that a method of setting an edge thickness in a 45° direction of a lens to the same edge thickness as an edge thickness of the rotationally symmetric lens has been proposed in the past. However, the edge thickness can be calculated only after parameters of the toric surface are determined. On the other hand, in the designing method using Expression (6) of this embodiment, it is unnecessary to calculate the edge thickness if a coefficient of $X^{2j}Y^{2(n-j)}$ (where j is a natural number other than n) is set to 0 or $a_{2qx}=-a_{2qy}$, $a_{2qx}a_{2py}=0$ (p and q are natural numbers). It is possible to design a shape having the edge thickness in the 450 direction equivalent to the edge thickness of the rotationally symmetric lens.

When a lens is manufactured by a so-called molding method, it is necessary to consider a change in a lens shape due to contraction of a lens material. By designing the lens using Expression (6) in this embodiment, if a base shape of the lens is the same as the shape of the rotationally symmetric lens, a contraction percentage can be regarded as equivalent to the contraction percentage of the rotationally symmetric lens. Therefore, according to the lens designing method in this embodiment, it is possible to more efficiently evaluate the contraction percentage than a conventional method for evaluating the contraction percentage with the toric intraocular lens, which is a non-rotationally symmetric lens.

Since paraxial curvatures in the X direction and the Y direction can also be easily calculated as explained below, calculation of paraxial refractive power is also easy. Therefore, it is possible to easily calculate paraxial power from the function of Expression (6). By using Expression (6), it is possible to control spherical aberrations in the X direction and the Y direction of the toric intraocular lens. By performing the lens deign using Expression (6) in this way, a As it is seen from Expression (7), if Expression (6) is used, a sectional shape in any direction (any θ) on the lens surface can be represented by a general optical surface definitional equation. It is possible to easily perform comparison with a design value and an optical simulation in any cross section of an actually manufactured lens.

An example in which the toric intraocular lens is designed using the premise technique of the present invention by using one of Expressions (6) and (7) is explained. Note that, in this explanation, a toric surface is formed as an optical surface of a ridge type (convex upward).

FIGS. 1A to 1C are schematic diagrams illustrating an example of an optical portion 100 of a conventional toric intraocular lens. Note that, in FIGS. 1A to 1C, illustration of a supporting portion of the toric intraocular lens is omitted. In the optical portion 100 illustrated in FIGS. 1A to 1C, it is assumed that an XY plane orthogonal to the optical axis of the optical portion is set and an X axis and a Y axis are orthogonal to each other. A Z axis orthogonal to the XY plane is set. Thickness in a Z-axis direction at an edge of the optical portion corresponds to an edge thickness.

FIG. 1A and FIG. 1B are side views of the optical portion 100. FIG. 1C is a view of the optical portion 100 viewed from a negative side of the Z axis, that is, an optical surface 104 side toward a positive side of the Z axis, that is, an optical surface 103 side.

As illustrated in FIG. 1C, on both surfaces of the optical portion 100 of the conventional toric intraocular lens, optical surfaces 103 and 104 are formed over the entire regions on the XY plane, that is, regions from a lens center 101 (the origin O of the XY plane) to an edge 102. In this embodiment, the optical surface 103 has a spherical shape or an aspherical shape and does not have a toric surface. On the other hand, the optical surface 104 is a toric surface. As illustrated in FIG. 1A, at the edge 102 of the optical portion 100, a thin portion 105 having a small edge thickness compared with an edge thickness of other portions is formed. A direction in which the thin portion 105 is formed when viewed from the lens center 101 corresponds to an extending direction of a so-called steep meridian. Note that the steep meridian overlaps the X axis in FIG. 1C.

Figure 2:
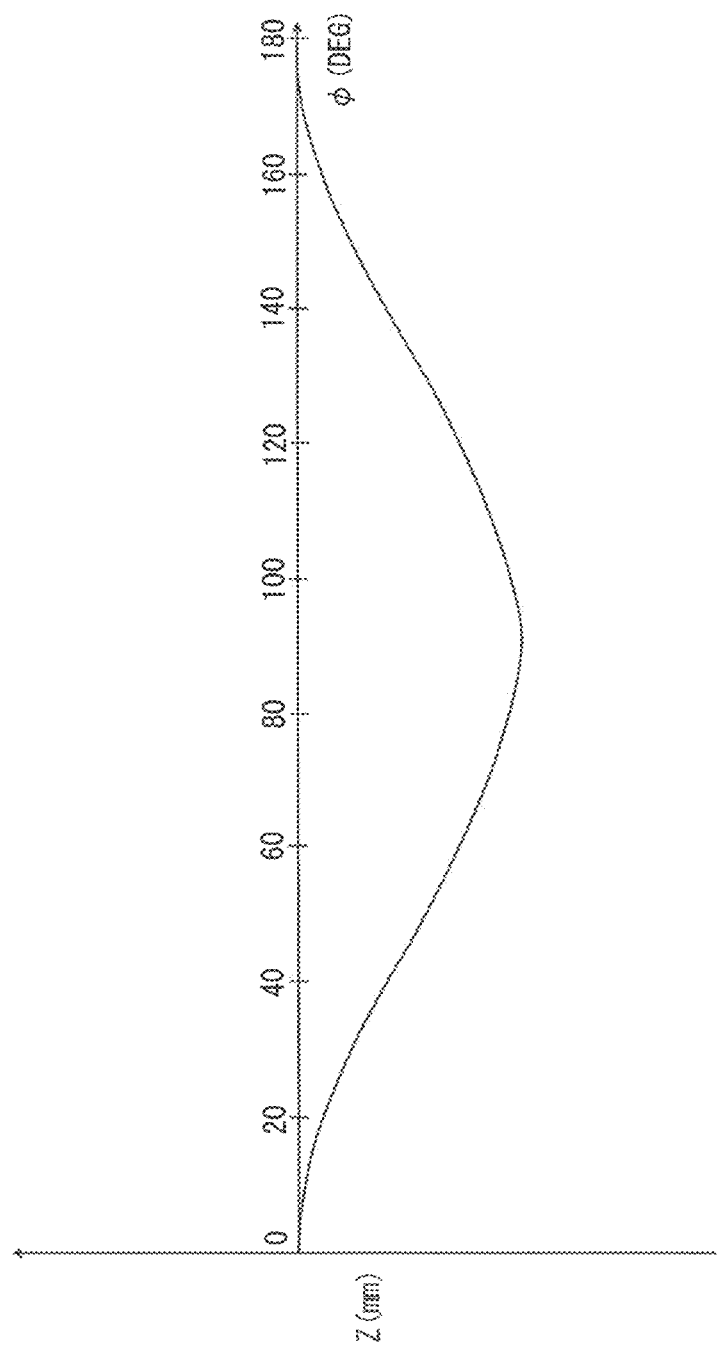
FIG. 2 is a graph illustrating an example of a change in an edge thickness of the conventional toric intraocular lens.

In FIG. 2, an example of a change in the edge thickness in an angle direction viewed from the lens center 101 of the optical portion 100 is illustrated. A vertical axis Z (mm) indicates a sag on the optical surface 104. In a graph of FIG. 2, a direction in which an angle ($\phi$; unit: °) of a horizontal axis is 0° and 180° is a flat meridian direction of the optical portion 100. A direction in which the angle is 90° is a steep meridian direction of the optical portion 100. A change in the edge thickness in a range in which the angle is 180° to 360° is the same as a change in the edge thickness in a range in which the angle is 0° to 180°. As illustrated in FIG. 2, the edge thickness of the optical portion 100 is the smallest in the steep meridian direction.

Therefore, in the case of lens design for providing a supporting portion in the thin portion 105, the supporting portion is connected to a portion having a small edge thickness. Therefore, there is a concern that a force for pressing the optical portion against a posterior capsule cannot be stably obtained. It is likely that the lens design is not considered to be desirable lens design from the viewpoint of preventing a secondary cataract.

Figure 3A:
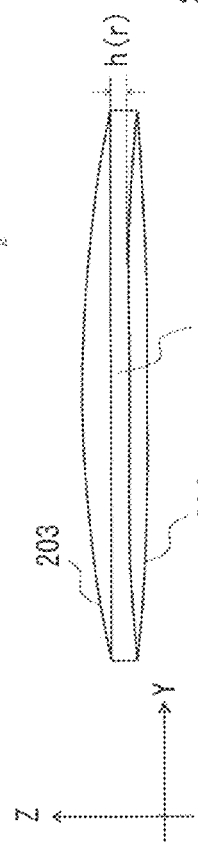
FIG. 3A is a first schematic diagram illustrating an example of a toric intraocular lens according to an embodiment.
Figure 3B:
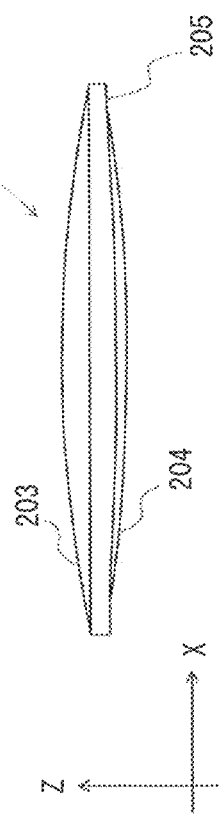
FIG. 3B is a second schematic diagram illustrating an example of a toric intraocular lens according to an embodiment.
Figure 3C:
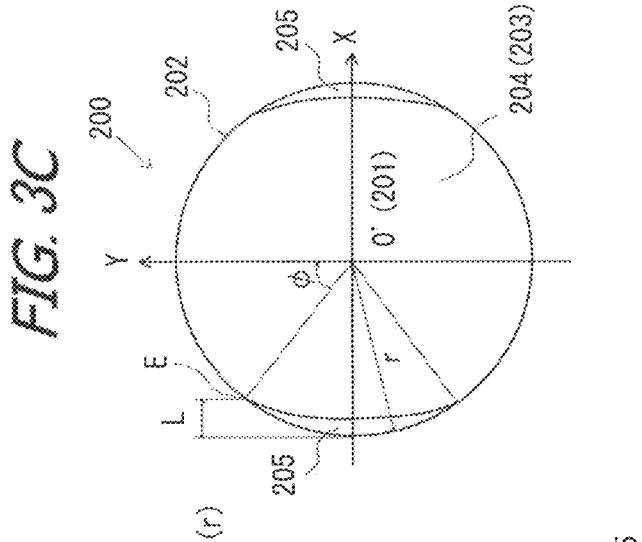
FIG. 3C is a third schematic diagram illustrating an example of a toric intraocular lens according to an embodiment.

On the other hand, an example of an optical portion 200 of the toric intraocular lens according to this embodiment is schematically illustrated in FIGS. 3A to 3C. As in FIGS. 1A to 1C, in FIGS. 3A to 3C, illustration of the supporting portion of the toric intraocular lens is omitted. As in the optical portion 100, in the optical portion 200, it is assumed that an XY plane orthogonal to the optical axis of the optical portion is set and an X axis and a Y axis are orthogonal to each other. A Z axis orthogonal to the XY plane is set. Thickness in a Z-axis direction at an edge of the optical portion corresponds to the edge thickness. FIG. 3A and FIG. 3B are side views of the optical portion 200. FIG. 3C is a view of the optical portion 200 viewed from a negative side of the Z axis, that is, an optical surface 204 side toward a positive side of the Z axis, that is, an optical surface 203 side. Note that, in FIGS. 3A to 3C, as in FIGS. 1A to 1C, the optical surface 203 has a spherical shape or an aspherical shape and does not have a toric surface. On the other hand, the optical surface 204 is a toric surface.

In the optical portion 200 of the toric intraocular lens in this embodiment, a center thickness in a lens center 201 (an origin O' of the XY plane) is equivalent to a center thickness in the lens center 101 of the optical portion 100 of the conventional toric intraocular lens. However, a substantially flat portion (hereinafter referred to as "flat portion") 205 having a substantially fixed edge thickness is formed at an edge 202. The flat portion 205 is formed to include an edge overlapping a steep meridian when viewed from the lens center 201. Note that, as in FIG. 1C, in FIG. 3C, the steep meridian overlaps the X axis. Therefore, in this embodiment, as illustrated in FIG. 3C, at the edge 202, two flat portions 205 are formed around one lens surface 204 of the optical portion 200. The flat portions 205 are formed to overlap the X axis and sandwich the lens center 201 in a top view of the optical portion 200. Note that the flat portion 205 is an example of the surface continuous to the edge of the optical portion and the toric surface of the optical portion in a top view of the optical portion.

As illustrated in FIG. 3A, an edge thickness in a position of a radius r from the lens center 201 in the flat portion 205 is represented as h(r). By appropriately deciding h(r), a range of an angle $\phi$ in which the flat portion 205 is formed viewed from the lens center 201 and width L of the flat portion 205 in an X-axis direction (a radial direction of the optical portion) are decided in a top view of the optical portion 200 illustrated in FIG. 3C. (Since the toric surface of the optical surface 204 is defined, if the edge thickness h(r) is decided, an intersection line of the toric surface of the optical surface 204 and a plane of the flat portion 205 is decided.) In this embodiment, as an example, a minimum edge thickness H in the flat portion 205 is set to satisfy 0.01 mm≤H–(high)≤0.05 mm. Concerning a region where the edge thickness h(r) is smaller than H, h(r) may be set to satisfy h(r)=H. In this embodiment, the toric lens flat portion 205 is provided such that the shape of the toric lens flat portion 205 is symmetrical with respect to the X axis, that is, the steep meridian.

In this embodiment, as explained above, if the edge thickness h(r) in the flat portion 205 is decided, the plane shape of the flat portion 205 is decided. However, in this embodiment, the plane shape of the flat portion 205 may be decided first (preferentially). For example, the angle $\phi$ at an end portion E of the flat portion 205 may be set to satisfy 55°≤$\phi$≤80°. Then, a range of an angle (an angle width) in which the flat portion is formed viewed from the lens center of the toric intraocular lens is 20° to 70° across the steep meridian (10° to 35° on one side with respect to the steep meridian). The width L in the X-axis direction of the flat portion 205 may be set to satisfy 0.05 mm≤L≤0.5 mm. In general, an optical portion diameter of an intraocular lens is $\phi$5 mm to 7 mm. Therefore, in the top view of the toric ophthalmic lens, the width L of the flat portion in a direction from the edge toward the lens center of the toric ophthalmic lens may be set to satisfy a condition (1/100 of the optical portion diameter)≤L≤(1/10 of the optical portion diameter). In these cases, the edge thickness h(r) is decided by determining a range of an angle (an angle width) of the flat portion 205 or the width L of the flat portion 205.

The edge thickness h(r) in the flat portion 205 is set to be smaller than an edge thickness on the flat meridian side of the optical portion 200 and larger than an edge thickness of the flat portion 205 formed as the toric surface of the optical portion 100. By setting the edge thickness h(r) in this way, the edge thickness on the flat meridian side of the optical portion 200, that is, an edge thickness of a portion overlapping the Y axis can be set the same as the edge thickness in the conventional optical portion 100. Therefore, according to this embodiment, only the edge thickness of the flat portion 205 is controlled and control of edge thicknesses of the other portions does not have to be considered. Therefore, it is easy to control the edge thickness of the flat portion 205 of the optical portion 200.

Figure 4:
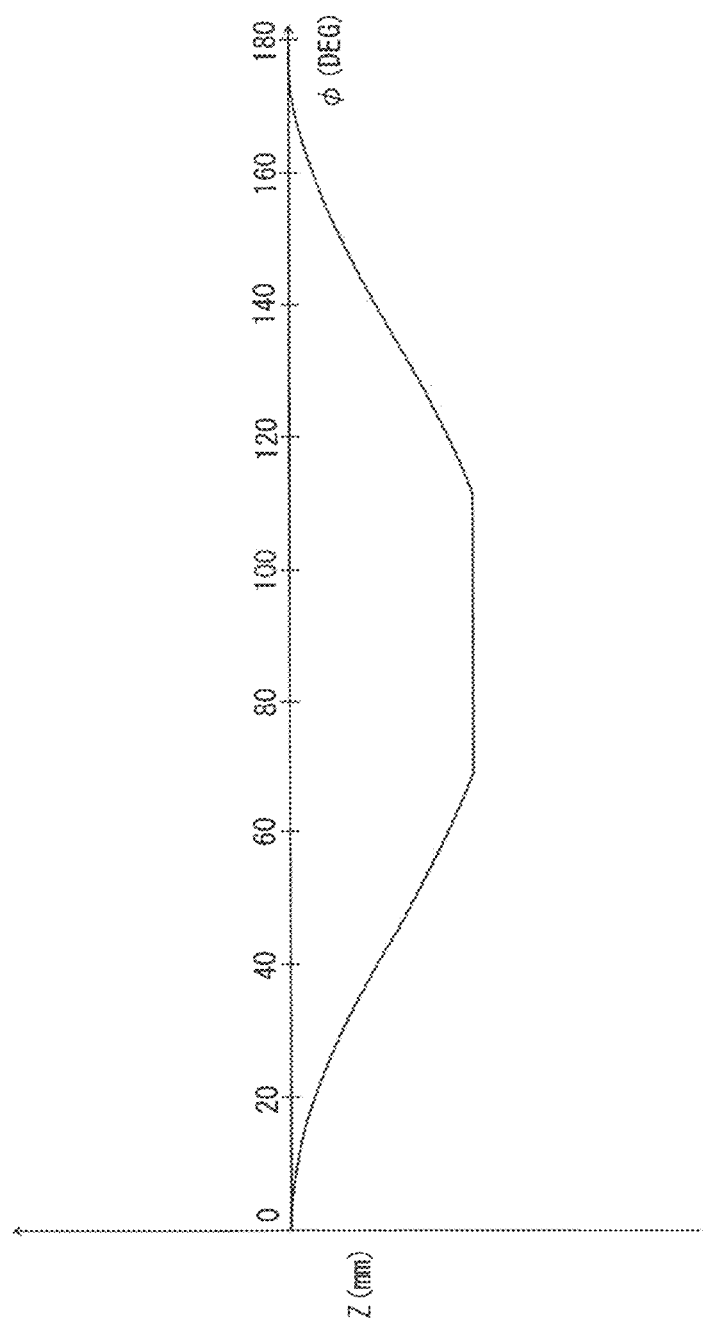
FIG. 4 is a graph illustrating an example of a change in an edge thickness of the toric intraocular lens according to the embodiment.

An example of a change in an edge thickness in an angle direction viewed from the lens center 201 of the optical portion 200 is illustrated in FIG. 4. In a graph of FIG. 4, an angle ($\phi$; unit: °) of a horizontal axis and a sag (Z; unit: mm) of a vertical axis are the same as those in FIG. 4. In the example illustrated in FIG. 4, the edge thickness of the optical portion 200 is fixed in a range of 70° to 110° across the steep meridian direction ($\phi$=90°). That is, the flat portion 205 is formed in this range. Note that, in the example illustrated in FIG. 4, the angle $\phi$ in FIG. 3C is 70°.

Therefore, in the case of lens design in which the supporting portion is provided in the flat portion 205, unlike the lens design in which the supporting portion is provided in the thin portion 105 of the optical portion 100, the edge thickness is secured as a predetermined thickness. Therefore, a force of the supporting portion pressing the optical portion against the posterior capsule is stably obtained. The lens design contributes to prevention of a secondary cataract.

In this embodiment, when the optical portion 200 of the toric intraocular lens is designed using one of Expressions (6) and (7) described above, conditions by the following Expressions (8) and (9) are added.

[Math. 10]

$$h(r) \geq H \quad (8)$$

[Math. 11]

$$H(\text{High}) \leq H < H(\text{Low}) \quad (9)$$

That is, in this embodiment, when the optical portion 200 of the toric intraocular lens is designed using one of Expressions (6) and (7) described above, in the region where the edge thickness $h(r)$ is smaller than $H$, $h(r)$ is set to satisfy $h(r)=H$. $H(\text{High})$ is an edge thickness of a portion overlapping the steep meridian (the X axis in the figure) of the optical portion 200 designed as the conventional optical portion 100. $H(\text{Low})$ is an edge thickness of a portion overlapping the flat meridian (the Y axis in the figure) of the optical portion 200 designed as the conventional optical portion 100. $H$ is equivalent to the predetermined minimum thickness.

In the configuration of the optical portion of the conventional toric intraocular lens, when the edge thickness decreases, it is likely that designing of the toric intraocular lens is hindered from the viewpoint of secondary cataract prevention. However, according to this embodiment, by designing the optical portion 200 using one of Expressions (6) and (7) based on the conditions described above, it is possible to realize the optical portion of the toric intraocular lens further contributing to the secondary cataract prevention than in the past.

The toric intraocular lens in this embodiment may be manufactured by a molding method or a cutting method. However, machining of the toric surface is desirably performed by a lathe capable of moving a machining tool in an optical axis direction while synchronizing the machining tool with rotating speed. Note that, in this embodiment, the example is explained in which the optical surface 204 is the toric surface and the optical surface 203 is the spherical surface or the aspherical surface. However, the configurations of optical surfaces to which the present invention is applied are not limited to this. The optical surface 204 may include an aspherical toric surface. Both of the optical surface 203 and the optical surface 204 may include toric surfaces. When both of the optical surface 203 and the optical surface 204 are toric surfaces and the steep meridian is common to the optical surface 203 and the optical surface 204, the edge thickness $h(r)$ is a difference between the thickness in the steep meridian of the optical surface 203 and the thickness of the flat portion 205.

The above is the explanation concerning this embodiment. However, the configuration of the toric intraocular lens is not limited to the embodiment explained above. Various changes are possible within a range in which identity with the technical idea of the present invention is not lost. For example, in the design of the toric intraocular lens explained above, as indicated by modifications explained below, expressions other than Expressions (6) and (7) described above may be used. In that case, the conditions indicated by Expressions (8) and (9) described above may be added and set. The ranges of the respective values of the angle φ, the width L, and the edge thickness $h(r)$ in the embodiment explained above are only examples and are not meant to limit the values to the ranges explained above. Further, in the embodiment explained above, in the top view of the optical portion 200, the flat portion 205 is formed to be symmetrical with respect to the X axis. However, the flat portion 205 does not have to be symmetrical with respect to the X axis if the flat portion 205 is formed to overlap the steep meridian (the X axis) of the toric surface of the optical portion 200. The portion of the flat portion 205 may be formed as a gentle inclined surface or a curved surface or a form obtained by combining the inclined surface and the curved surface.

With such a designing method for the toric intraocular lens, it is possible to design the toric intraocular lens in which, in the top view of the optical portion, the surface (the flat portion 205) continuous to the edge of the optical portion and the toric surface of the optical portion is provided, the edge thickness of the optical portion on the continuous surface is substantially fixed, and the continuous surface is provided to overlap the steep meridian of the toric surface of the optical portion.

Modifications of the embodiment indicated above are explained below. In the following explanation, a steep meridian direction of a toric intraocular lens is set as an X direction and a flat meridian direction of the toric intraocular lens is set as a Y direction. However, X and Y may be opposite. Note that details of derivation of expressions explained below are described in the patent literatures described above. Therefore, explanation of the details is omitted. Examples of expressions for defining the conventional toric surface include Expression (10) representing a shape of a lens cross section by a plane including an X axis and an optical axis and Expression (11) representing a lens cross section by a plane including a Y axis and the optical axis. In the expressions, Rx and Ry respectively represent a curvature radius of the lens cross section by the plane including the X axis and the optical axis and a curvature radius of the lens cross section by the plane including the Y axis and the optical axis. Note that Rx≠Ry. In the expressions, cx and cy respectively represent a curvature of the lens cross section by the plane including the X axis and the optical axis and a curvature of the lens cross section by the plane including the Y axis and the optical axis, where cx=1/Rx and cy=1/Ry. In the expressions, kx and ky respectively represent a conic constant in the X direction and a conic constant in the Y direction. Note that there is the description of kx≠ky in PTL 4 (Japanese Patent No. 4945558).

[Math. 12]

$$Z_x = \sqrt{2R_x x - (1+k_x)x^2} \quad (10)$$

[Math. 13]

$$Z_y = \sqrt{2R_y y - (1+k_y)y^2} \quad (11)$$

Examples of expressions used for design of the conventional toric intraocular lens include Expressions (12) and (13) instead of Expressions (10) and (11). Note that Rx≠Ry. There is the description of kx≠ky in Japanese Patent No. 4945558.

[Math. 14]

$$Z_x = \frac{x^2/R_x}{1+\sqrt{1-(1+k_x)x^2/R_x^2}} + \sum_j c_j x^j \quad (12)$$

[Math. 15]

$$Z_y = \frac{y^2/R_y}{1+\sqrt{1-(1+k_y)y^2/R_y^2}} + \sum_j c_j y^j \quad (13)$$

When Expressions (10) and (11) or Expressions (12) and (13) are used, shapes of lens cross sections in the X direction and the Y direction can only be defined and a sectional shape of the entire lens cannot be defined.

Alternatively, there is also a method of designing the toric intraocular lens using Expression (14).

[Math. 16]

$$Z(r,\theta) = \frac{(c_x\cos^2\theta + c_y\sin^2\theta)r^2}{1+\sqrt{1-(1+k_x)c_x^2r^2\cos^2\theta - (1+k_y)c_y^2r^2\sin^2\theta}} \quad (14)$$

When the toric intraocular lens is designed using Expressions (10) to (14) described above, the edge thickness in the steep meridian direction of the optical portion is secured at the predetermined thickness as in the embodiment described above by adding the condition of Expressions (8) and (9) to design the toric intraocular lens. Consequently, it is possible to perform lens design contributing to prevention of a secondary cataract.

Figure 5:
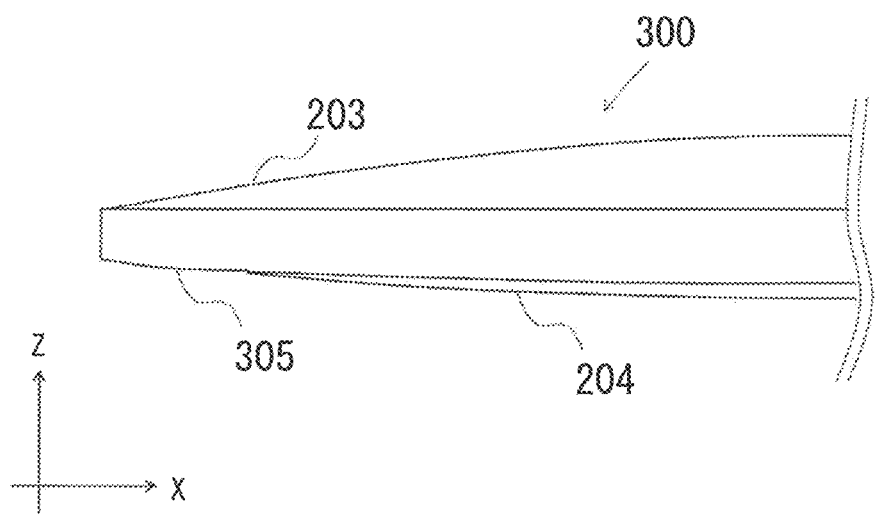
FIG. 5 is a schematic diagram illustrating an example of a toric intraocular lens according to a modification.
Figure 6:
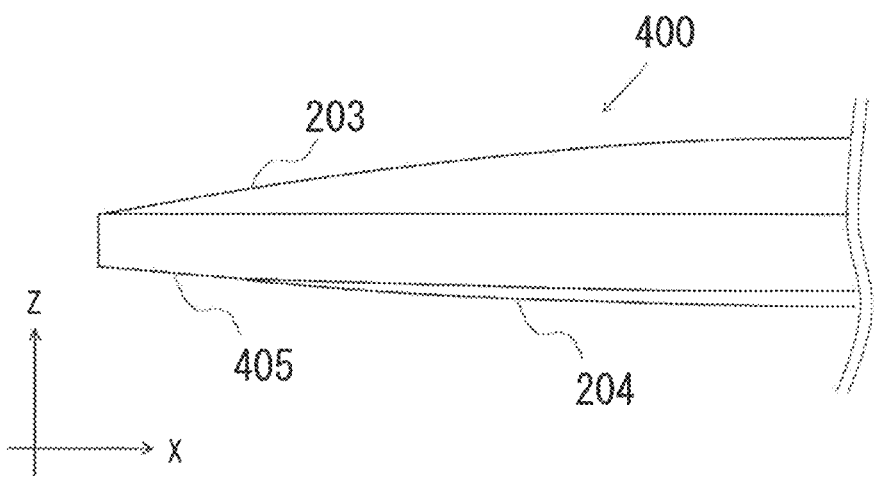
FIG. 6 is a schematic diagram illustrating an example of a toric intraocular lens according to another modification.

Partially enlarged views showing schematic configurations of toric intraocular lenses 300 and 400 according to the modifications of the embodiment explained above are illustrated in FIGS. 5 and 6. Note that components not illustrated in FIGS. 5 and 6 are the same as the components of the toric intraocular lens 200 explained above. Therefore, illustration and detailed explanation of the components are omitted. In the toric intraocular lenses 300 and 400 according to the modifications, a curved surface portion 305 and an inclined portion 405 are respectively formed instead of the flat portion 205 of the toric intraocular lens 200 explained above. Like the flat portion 205 explained above, the curved surface portion 305 and the inclined portion 405 are not portions formed for the purpose of exerting an aberration correcting function of the toric intraocular lens unlike the optical surface 204. In this regard, not only the flat portion 205 explained above but also the inclined portion 405 can be considered to be the portion including the surface continuous to the edge of the optical portion and the toric surface of the optical portion. Further, the curved surface portion 305 including a surface different from the optical surface 204 in terms of an optical function can also be considered to be the portion including the surface continuous to the edge of the optical portion and the toric surface of the optical portion.

In this way, when the toric intraocular lens 300 in which the curved surface portion 305 is formed or the toric intraocular lens 400 in which the inclined portion 405 is formed is adopted, as in the toric intraocular lens 200, the edge thickness is secured at the predetermined thickness. Therefore, a force of the supporting portion pressing the optical portion against the posterior capsule can be stably obtained. Lens design contributes to prevention of a secondary cataract.

Further, with the designing methods for the toric intraocular lenses 200, 300, and 400, it is also possible to expect an effect that the center thickness of the optical portion can be set smaller than the center thickness in the design of the conventional toric intraocular lens 100 when the edge thickness is determined. That is, with the designing method according to the embodiment explained above, even if the center thickness of the optical portion is set smaller than the center thickness in the design of the conventional toric intraocular lens, it is considered possible to secure the edge thickness explained above.

REFERENCE SIGNS LIST

200 Optical portion
202 Edge
205 Flat portion

What is claimed is:

1. A toric ophthalmic lens comprising an optical portion, wherein
   the optical portion comprises two optical surfaces and an edge lying between the two optical surfaces in a side view of the optical portion,
   at least one of the two optical surfaces includes a toric surface and the toric ophthalmic lens includes a substantially flat portion, the substantially flat portion having a substantially constant edge thickness, and the toric surface comprises a steep meridian and a flat meridian, and
   in a top view of the optical portion, the substantially flat portion is provided adjacent to the edge of the optical portion such that the substantially flat portion does not overlap the flat meridian of the toric surface but overlaps the steep meridian of the toric surface, and further, an intersection line is formed at a boundary between the toric surface and the substantially flat portion, and in a top view of the optical portion, the edge of the substantially flat portion overlaps a substantial portion of the optical portion, and
   a portion of the toric ophthalmic lens other than the substantially flat portion extends from an edge of the lens along the flat meridian to an opposite edge of the lens and the portion of the toric ophthalmic lens other than the substantially flat portion extends substantially across the steep meridian but does not extend to an edge portion of the lens where the substantially flat portion is formed.

2. The toric ophthalmic lens according to claim 1, wherein the edge thickness of the substantially flat portion is smaller than an edge thickness of the optical portion at the flat meridian of the toric surface, and wherein the edge thickness of the substantially flat portion is larger compared to an edge thickness of an optical portion in proximity to a steep meridian of a toric surface of a toric ophthalmic lens which does not have a substantially flat portion.

3. The toric ophthalmic lens according to claim 1, wherein the substantially flat portion is formed by replacing a region of the toric surface where an edge thickness is smaller than a predetermined thickness in the toric ophthalmic lens with a flat portion so that the edge thickness of the region equals the predetermined thickness.

4. A toric ophthalmic lens comprising an optical portion, wherein
   the optical portion comprises two optical surfaces and an edge lying between the two optical surfaces in a side view of the optical portion, at least one of the two optical surfaces includes a toric surface and the toric ophthalmic lens includes a substantially flat portion, the substantially flat portion having a substantially constant edge thickness, and in a top view of the optical portion, the edge of the substantially flat portion overlaps a substantial portion of the optical portion, and in a top view of the optical portion, an edge thickness h(r) of the optical portion which a radius of the optical portion is r satisfies Expression (1) in any portion of the edge of the optical portion and an edge thickness H representing an edge thickness of the substantially flat portion provided adjacent to the edge of the optical portion satisfies Expression (2),

[Math. 1]

$$h(r) \geq H \quad (1)$$

[Math. 2]

$$H(\text{High}) < H < H(\text{Low}) \quad (2)$$

wherein, H(High) represents an edge thickness in proximity to a steep meridian of a toric ophthalmic lens which does not have a substantially flat portion, and H(Low) represents an edge thickness at a flat meridian of the toric ophthalmic lens, a portion of the toric ophthalmic lens other than the substantially flat portion extends from an edge of the lens along the flat meridian to an opposite edge of the lens and the portion of the toric ophthalmic lens other than the substantially flat portion extends substantially across the steep meridian but does not extend to an edge portion of the lens where the substantially flat portion is formed.

5. The toric ophthalmic lens according to claim 4, wherein a sectional shape in any meridian direction on a lens surface of the toric ophthalmic lens is represented by an expression including:

[Math. 3]

$$Z = \frac{cr^2}{1 + [1 - c^2 r^2 (k+1)]^{1/2}} + A(\theta) r^2 + B(\theta) r^4 \quad (3)$$

wherein, c represents a paraxial curvature in the toric ophthalmic lens, r represents a distance from the lens center of the toric ophthalmic lens, k represents a conic constant of a surface rotationally symmetrical to a lens optical axis in the toric ophthalmic lens, c, r, and k are common concerning the meridian direction on the lens surface, and A(θ) and B(θ) are given by Expressions (4) and (5):

[Math. 4]

$$A(\theta) = a_{2x} \cos^2 \theta + a_{2y} \sin^2 \theta \quad (4)$$

[Math. 5]

$$B(\theta) = a_{4x} \cos^4 \theta + a_{2x2y} \cos^2 \theta \sin^2 \theta + a_{4y} \sin^4 \theta \quad (5)$$

wherein $a_{2x}$, $a_{2y}$, $a_{4x}$, $a_{2x2y}$, and $a_{4y}$ represent parameters for adding a toric surface and $a_{2x}$, $a_{2y}$, $a_{4x}$, $a_{2x2y}$, and $a_{4y}$ are not 0.

6. The toric ophthalmic lens according to claim 1, wherein, in a top view of the toric ophthalmic lens, width of the substantially flat portion in a direction from an edge toward a lens center of the toric ophthalmic lens is 0.05 mm or more and 0.5 mm or less.

7. The toric ophthalmic lens according to claim 1, wherein, in a top view of the toric ophthalmic lens, width of the substantially flat portion in a direction from an edge toward a lens center of the toric ophthalmic lens is 1/100 or more of an optical portion diameter and 1/10 or less of the optical portion diameter.

8. The toric ophthalmic lens according to claim 1, wherein, in a top view of the toric ophthalmic lens, a range of an angle in which the substantially flat portion is formed viewed from a lens center of the toric ophthalmic lens is 20° or more and 70° or less across the steep meridian.

9. A toric ophthalmic lens comprising an optical portion, wherein the optical portion comprises two optical surfaces and an edge lying between the two optical surfaces in a side view of the optical portion, at least one of the two optical surfaces includes a toric surface and the toric ophthalmic lens includes a continuous surface, and in a top view of the optical portion, the continuous surface contiguous to an edge of the optical portion and the toric surface of the optical portion and in a top view of the optical portion, the edge of the continuous surface overlaps a substantial portion of the optical portion, and an edge thickness of the continuous surface is substantially constant, and the toric surface comprises a steep meridian and a flat meridian, the continuous surface is provided not to overlap the flat meridian of the toric surface of the optical portion and provided to overlap the steep meridian of the toric surface, and further, an intersection line is formed at a boundary between the toric surface and the continuous surface, a portion of the toric ophthalmic lens other than the continuous surface extends from an edge of the lens along the flat meridian to an opposite edge of the lens and the portion of the toric ophthalmic lens other than the continuous surface extends substantially across the steep meridian but does not extend to an edge portion of the lens where the continuous surface is formed.

\* \* \* \* \*

UNITED STATES PATENT AND TRADEMARK OFFICE
CERTIFICATE OF CORRECTION

| | | |
|---|---|---|
| PATENT NO. | : 11,366,336 B2 | |
| APPLICATION NO. | : 16/467473 | |
| DATED | : June 21, 2022 | |
| INVENTOR(S) | : Haruo Ishikawa | |

It is certified that error appears in the above-identified patent and that said Letters Patent is hereby corrected as shown below:

In the Claims

Column 14, Line 34 (approx.), Claim 9, after "surface" insert -- is provided --.

Signed and Sealed this
Tenth Day of January, 2023

*Katherine Kelly Vidal*

Katherine Kelly Vidal
*Director of the United States Patent and Trademark Office*